United States Patent [19]
Urrutia

[11] Patent Number: 6,017,332
[45] Date of Patent: Jan. 25, 2000

[54] MEDICAL DYE DELIVERY SYSTEM

[76] Inventor: Hector Urrutia, 2404 W. Augusta Sq., McAllen, Tex. 78503

[21] Appl. No.: 08/954,661

[22] Filed: Oct. 20, 1997

[51] Int. Cl.[7] ...................................................... A61M 5/00
[52] U.S. Cl. ......................... 604/254; 604/246; 604/247; 137/192; 137/399
[58] Field of Search .................. 604/246, 30, 31, 604/247, 254, 256; 137/403, 433, 451, 399, 192

[56] References Cited

U.S. PATENT DOCUMENTS

| | | |
|---|---|---|
| 1,144,657 | 6/1915 | Keller . |
| 1,788,358 | 1/1931 | Goerg . |
| 2,214,290 | 9/1940 | Ward . |
| 2,924,237 | 2/1960 | Ellis . |
| 3,227,173 | 1/1966 | Bernstein ................................ 137/192 |
| 3,790,306 | 2/1974 | Uefuji . |
| 4,096,079 | 6/1978 | Serur et al. ............................. 137/391 |
| 4,208,881 | 6/1980 | Brademeyer et al. . |
| 4,323,173 | 4/1982 | Shannon . |
| 4,633,681 | 1/1987 | Webber . |
| 4,950,254 | 8/1990 | Andersen et al. ....................... 604/247 |
| 5,213,586 | 5/1993 | Welker . |
| 5,322,099 | 6/1994 | Langlois . |
| 5,373,957 | 12/1994 | Gryc . |
| 5,722,961 | 3/1998 | Fan ........................................... 604/254 |

FOREIGN PATENT DOCUMENTS

1138647  6/1957  France .

*Primary Examiner*—Corrrine McDermott
*Assistant Examiner*—Kent Gring
*Attorney, Agent, or Firm*—Oliff & Berridge, PLC

[57] ABSTRACT

A medical dye delivery system includes a medical dye container and a syringe for withdrawing the medical dye from the container and delivering the dye to a patient. A valve is disposed in the system having an inlet in flow communication with the medical dye container and an outlet in flow communication with the syringe. The valve includes a housing defining a flotation chamber with a valve seat and a flotation member disposed therein. The flotation member seals off the valve seat opening upon medical dye depletion, forcing any remaining fluid flow through a bypass channel that provides restricted flow to provide a tactile warning to the operator of the system that the medical dye container is depleted, yet allow the operator to purge remaining dye from the system.

25 Claims, 5 Drawing Sheets

MEDICAL DYE DELIVERY SYSTEM

BACKGROUND OF THE INVENTION

1. Field of Invention

This invention generally relates to a medical dye delivery system. More particularly, this invention relates to a system for delivering medical dye to a patient that minimizes the risk of introducing air into the dye delivery system.

2. Description of Related Art

Medical dye delivery systems are used by medical personnel to inject dye into a patient. The dye serves as a contrast medium for various diagnostic procedures, such as angiography. A medical dye delivery system generally includes a medical dye container that is connected in flow communication through a series of conduits to a mechanism for introducing dye into the patient. The mechanism draws the dye from the container and then directs the dye through the system and into the patient.

When performing diagnostic tests on a patient using the medical dye delivery system, the operator generally focuses on a visual display of the patient on a monitor and not on the amount of dye in the dye delivery system. This can cause the operator to unknowingly deplete the dye container, thereby drawing air into the system. To purge this air requires a time consuming effort. If the air is not purged, it may enter the patient and cause an embolism or other harmful effects. Further, the entrance of air in the system often occurs at a critical time of the procedure when even minor delays can have undesirable consequences.

Typical angiography procedures require between 80 cc and 300 cc of medical dye. In addition, the medical dye is typically sold in containers holding 50 cc, 100 cc, or 150 cc, with 100 cc bags being the most common. Because two or more containers may be required for an angiography procedure, the operator must be quickly made aware of when one container has been depleted to quickly switch to another, full container.

SUMMARY OF THE INVENTION

Accordingly, the present invention is directed to a medical dye delivery system that substantially obviates one or more of the problems due to limitations and disadvantages of the related art.

To achieve these and other advantages and in accordance with the purpose of the invention, as embodied and broadly described, the invention includes a medical dye container and a device for withdrawing medical dye from the container and directing the medical dye through a system flow path into a patient. A valve is disposed in the system, having an inlet in flow communication with the medical dye container and an outlet in flow communication with the withdrawing device. The valve includes a housing defining a chamber adapted for containing a volume of medical dye, a valve seat located in the chamber in flow communication with the outlet, and a flotation member. The flotation member is adapted for floating in the medical dye located in the chamber and is seated against the valve seat when the chamber is free of medical dye, thereby covering the valve seat opening.

The valve may also include a bypass channel in flow communication with the withdrawing device that is configured to provide restricted flow relative to flow through the valve seat opening when the medical dye is depleted. The restricted flow operates as a tactile warning to the operator that the medical dye is depleted and allows the operator to purge the remaining dye from the system flow path.

Additional features and advantages of the invention will be set forth in the description which follows, and in part will be apparent from the description, or may be learned by practice of the invention. The objectives and other advantages of the invention will be realized and attained by the apparatus particularly pointed out in the written description and claims hereof, as well as the appended drawings.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are incorporated in and constitute a part of this specification, illustrate embodiments of the invention and, together with the description, serve to explain the objects, advantages and principles of the invention. In the drawings.

DETAILED DESCRIPTION OF PREFERRED EMBODIMENTS

Reference will now be made in detail to the present preferred embodiments of the invention, examples of which are illustrated in the accompanying drawings.

Figure 1:
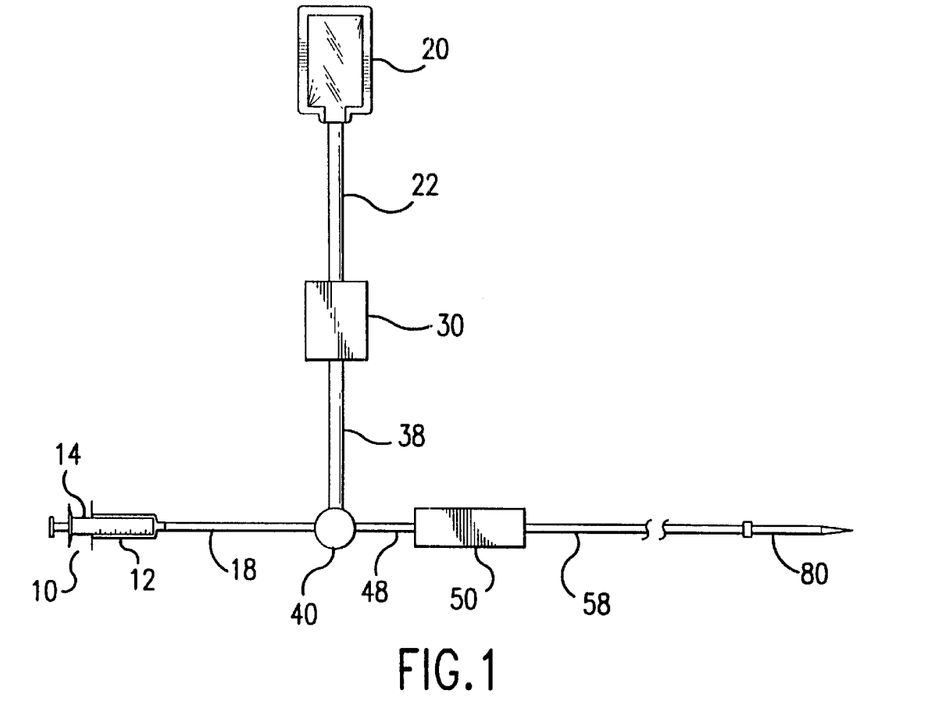
FIG. 1 is a diagram of a medical dye delivery system of the present invention.

A medical dye delivery system of the present invention is shown in FIG. 1. The system generally includes a medical dye container 20, a syringe 10 or other means for withdrawing medical dye from container 20 and directing the dye into the patient, a valve 30 for monitoring the level of medical dye in the system, a flow control valve 40 for regulating the flow of medical dye through the system, and a fluid delivery device 80 for channeling the medical dye into the patient. Optionally, a valve manifold 50 may be provided in the system to introduce alternative fluids into the patient prior to, during, or after the procedure. These components are connected in flow communication via a series of conduits to define a system flow path, as shown in FIG. 1, to deliver medical dye to the patient.

Medical dye container 20 may be a bag, bottle, or any other type of container that may be used for containing any of the medical dyes that are known in the art. The outlet of medical dye container 20 is connected through conduits 22 and 38 to a port of three-way flow control valve 40. A dye container air vent 24 (see FIG. 8) may be disposed near the outlet of container 20 to facilitate the flow of dye from container 20 and through the system.

A second port of flow control valve 40 is connected through a conduit 18 to syringe 10, and a third port of valve 40 is connected in flow communication with fluid delivery device 80 via conduits 48 and 58. Valve 40 selectively controls the flow of dye between container 20 and syringe 10 and between syringe 10 and delivery device 80, which may be any device for channeling medical dye into the patient, such as a needle, a cannula, or a catheter.

Control valve 40 may be a three-way valve having a valve element movable between at least two positions to direct flow. In the first position, the valve element operates to connect the first port of valve 40 in flow communication with the second port, but block flow through the third port. This position allows for medical dye to be drawn into syringe 10 from medical dye container 20, but prevents flow through delivery device 80. In the second position, the valve element connects the second port of valve 40 in flow communication with the third port, but blocks flow through the first port. This position allows for medical dye contained in syringe 10 to be injected into the patient via delivery device 80, but prevents back flow from syringe 10 to container 20.

Figure 2:
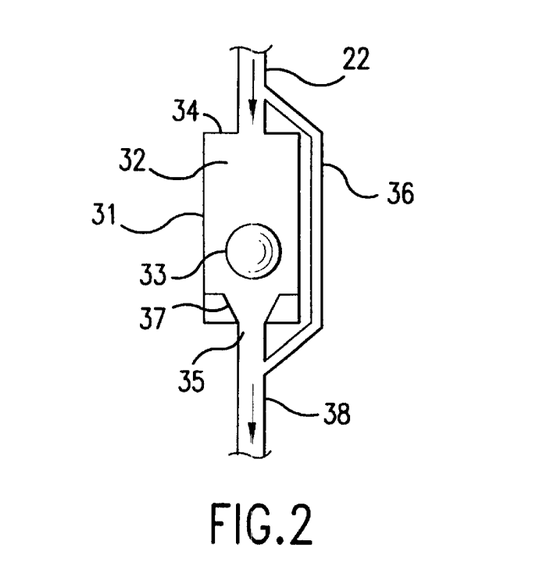
FIG. 2 is an elevation view of a valve for the medical dye delivery system shown in FIG. 1.

Valve 30 is disposed in the system flow path between container 20 and control valve 40 and is configured to alert the operator when medical dye container 20 is empty. As shown in FIG. 2, valve 30 includes a housing 31 enclosed at its top end by an inlet port 34 and at its bottom end by an outlet port 35. Inlet port 34 is connected through conduit 22 in flow communication with medical dye container 20 (FIG. 1). Outlet port 35 is connected through conduit 38 in flow communication with flow control valve 40 (FIG. 1).

Housing 31 also defines a flotation chamber 32, which acts as a reservoir for containing a volume of medical dye. A valve seat 37, having a substantially conical shape, is positioned in housing 31 and has an opening therethrough in flow communication with outlet port 35. A flotation member or ball 33, having a larger diameter than outlet port 35, is positioned in flotation chamber 32 and is adapted for floating in the volume of medical dye in flotation chamber 32. When flotation chamber 32 is empty of medical dye, flotation member 33 will seat on valve seat 37, thus blocking outlet port 35 and preventing the flow of air or other fluid therethrough.

To operate the medical dye delivery system, the operator sets control valve 40 so that container 20 is in flow communication with syringe 10. As shown in FIG. 1, syringe 10 includes a housing 12 and a plunger 14 that fits snugly within housing 12, forming a sliding fluid seal with the housing. When plunger 14 is withdrawn from housing 12, a vacuum is created, drawing medical dye through conduits 22, 38, and 18 and into syringe housing 12, and filling flotation chamber 32 with medical dye. Once syringe housing 12 contains medical dye, control valve 40 is set to connect syringe 10 in flow communication with delivery device 80, and prevent back flow between syringe and container 20. Syringe plunger 14 is then pushed into housing 12, forcing the medical dye through conduits 18, 48, and 58, and eventually into the patient via delivery device 80. These steps are repeated several times until sufficient dye is injected into the patient or the dye is depleted.

Prior to delivering dye to the patient, the system must be primed to expel air from the system flow path. However, since flotation chamber 32 of valve 30 is devoid of dye at this time, flotation member may seat against valve seat and block flow from container 20 to syringe 10. Thus, valve 30 must be manipulated so that flotation member 33 is not seated against valve seat 37 (e.g., valve is held in a horizontal orientation) while withdrawing plunger 14 from housing 12, thereby drawing the medical dye into valve 30. When sufficient medical dye enters flotation chamber 32, valve 30 can be returned to its normal vertical orientation.

When sufficient medical dye is in the system, flotation chamber 32 will contain sufficient medical dye to cause suspension of flotation member 33, thus allowing for unencumbered flow of medical dye through valve 30. However, when medical dye in medical dye container 20 is depleted, flotation chamber 32 will not contain sufficient medical dye to suspend flotation member 33. Flotation member 33 will then seat on valve seat 37, sealing the opening to outlet port 35 and preventing air from being drawn into the system through the dye container air vent by manipulation of syringe 10. Thus, valve 30 prevents the harmful effects associated with inadvertently injecting air into the patient.

When flotation member 33 becomes seated against valve seat 37, any dye remaining in conduits 38 and 18 cannot be drawn into syringe housing. However, the operator may desire to use this remaining medical dye to complete the procedure. To allow for the use of the remaining dye, valve 30 includes a bypass channel. When outlet port 35 is sealed by flotation member 33, air can be drawn through bypass channel, allowing the remaining fluid to be used. Bypass channel is configured to provide restricted flow through the system, thereby increasing the force necessary to draw fluid through the system with syringe 10. This gives the operator a tactile warning of the low volume of dye remaining in the system, but still allows the operator to use this remaining dye if so desired.

Various bypass channel configurations are shown in FIGS. 2–9. Unless otherwise noted, the previously-described components of valve 30 are identical for each of the embodiments.

Various other embodiments of the bypass channel, other than those disclosed, are contemplated so long as the bypass channel provides restricted flow through the system and provides a tactile warning of the low volume of dye remaining in the system.

In the embodiment shown in FIG. 2, bypass channel 36 has an inlet upstream of valve seat 37 and in flow communication with container 20 via conduit 22, and an outlet downstream of valve seat 37 and in flow communication with conduit 38. Thus, bypass channel 36 defines an alternate flow path between container 20 and control valve 40 that "bypasses" valve seat 37. While the bypass channel inlet shown in FIG. 2 is connected to conduit 22, it may also connect to housing 31 at any position above (i.e., upstream) of valve seat 37.

In this embodiment, the cross-section of bypass channel 36 is substantially smaller than the opening through valve seat 37, requiring the operator to use more force to draw the medical dye through bypass channel 36. "Substantially smaller," as used in this context, means small enough in comparison to the valve seat opening and port 35 to provide a noticeable difference in the force required to withdraw syringe plunger 14, thus providing a tactile warning to the operator that flotation member 33 is seated against valve seat 37. For example, the bypass channel diameter may be about 0.025–0.035 inches, while the valve seat opening is about 0.0625 inches or more.

Figure 3:
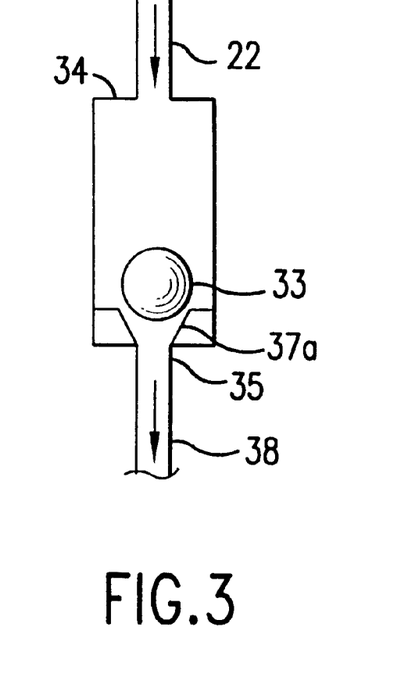
FIG. 3 is an elevation view of another embodiment of a valve for the medical dye delivery system shown in FIG. 1.
Figure 4:
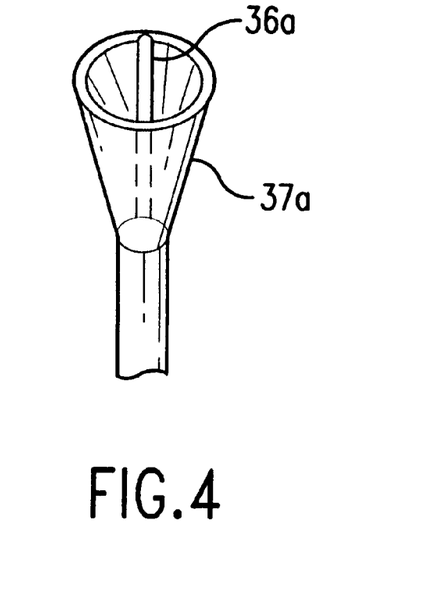
FIG. 4 is a perspective view of the valve shown in FIG. 3.

In another embodiment shown in FIGS. 3 and 4, bypass channel 36a is integrated into valve seat 37a, which is otherwise identical to valve seat 37 shown in FIG. 2. Thus, when medical dye container 20 is depleted, flotation member 33 will seat on valve seat 37*a*, but will not block slotted bypass channel 36*a*, thus permitting fluid to be drawn therethrough. Slotted bypass channel 36*a* has an opening substantially smaller than that of valve seat opening, and thus requires more force to draw the fluid through bypass channel 36*a*.

Figure 5:
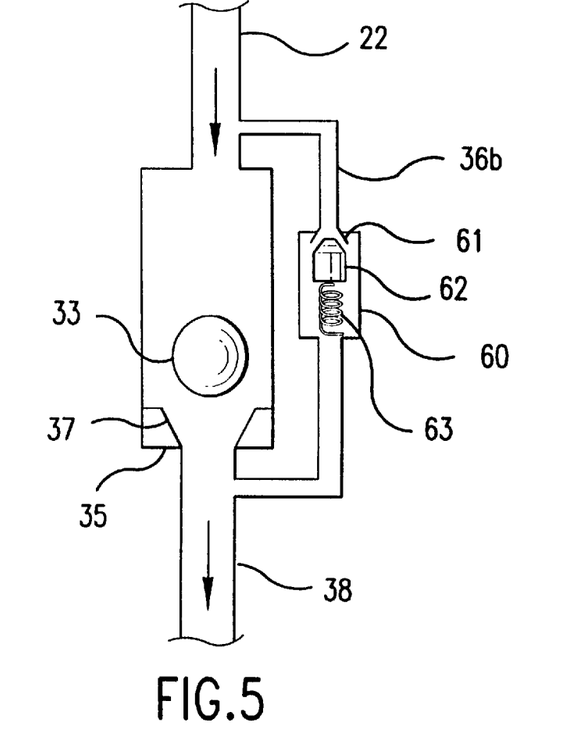
FIG. 5 is an elevation view of another embodiment of a valve for the medical dye delivery system shown in FIG. 1.

In another embodiment shown in FIG. 5, bypass channel 36*b* includes a bypass valve 80, including a valve seat 61 and a valve member 62 biased against valve seat 61 with a predetermined biasing force provided by a spring 63. When the opening through valve seat 37 is blocked by flotation member 33, the continued withdrawal by syringe 10 (FIG. 1) increases the suction force in the system. This increased suction force overcomes the predetermined biasing force provided by spring 63 and causes valve member 62 to become unseated form valve seat 61, thereby opening a fluid pathway through bypass channel 36*b*. The predetermined biasing force, which is preferably adjustable by the user, is selected so that it is sufficient to provide a tactile resistance that will alert the operator of the medical dye depletion, yet allow the operator to draw the remaining dye through the system. In this embodiment, the cross-section of the bypass channel is not critical since bypass valve 80 operates to provide the tactile resistance. However, a combination of a smaller bypass channel cross-section (relative to the valve seat opening diameter) and valve 80 may be used.

Figure 6:
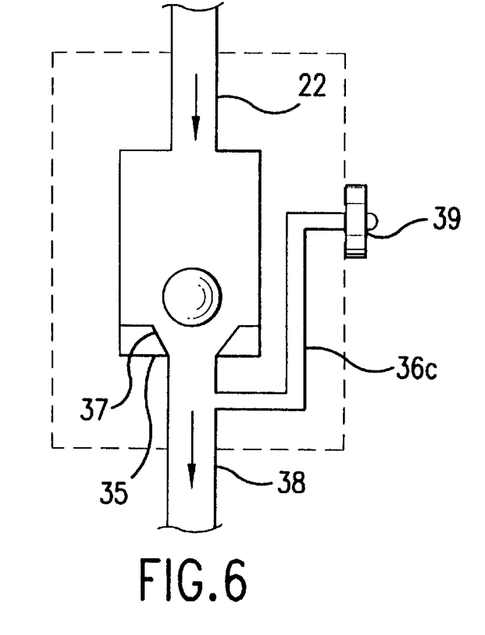
FIG. 6 is an elevation view of another embodiment of a valve for the medical dye delivery system shown in FIG. 1.

In another embodiment shown in FIG. 6, bypass channel 36*c* includes a first opening downstream of valve seat 37 and a second opening adjacent to an exterior wall of valve 30. A bypass valve 39 selectively allows external air to enter bypass channel 36*c* through the second opening. Bypass valve 39 may be a spring-biased valve similar to the one shown in FIG. 5, or may be a stopcock-like arrangement that the operator simply switches from a no-flow to a flow position when increased resistance, caused by the flotation member covering the valve seat opening, is detected.

Figure 7:
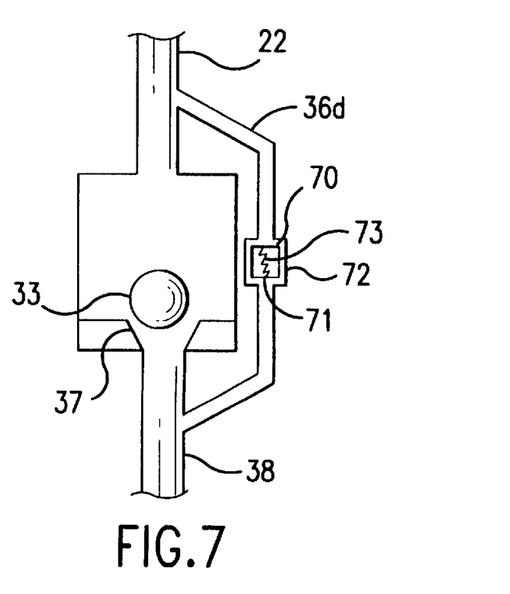
FIG. 7 is an elevation view of another embodiment of a valve for the medical dye delivery system shown in FIG. 1.

In another embodiment shown in FIG. 7, bypass channel 36*d* includes a bypass valve 70 including a flexible, fenestrated rubber piece 71 disposed in a bypass valve seat 72. Fenestrated rubber piece 71 is of the same diameter as bypass valve seat 72 and acts as a seal, forcing fluid through one or more openings 73 in rubber piece 71 that collectively have a substantially smaller area than the opening through valve seat 37.

Figure 8:
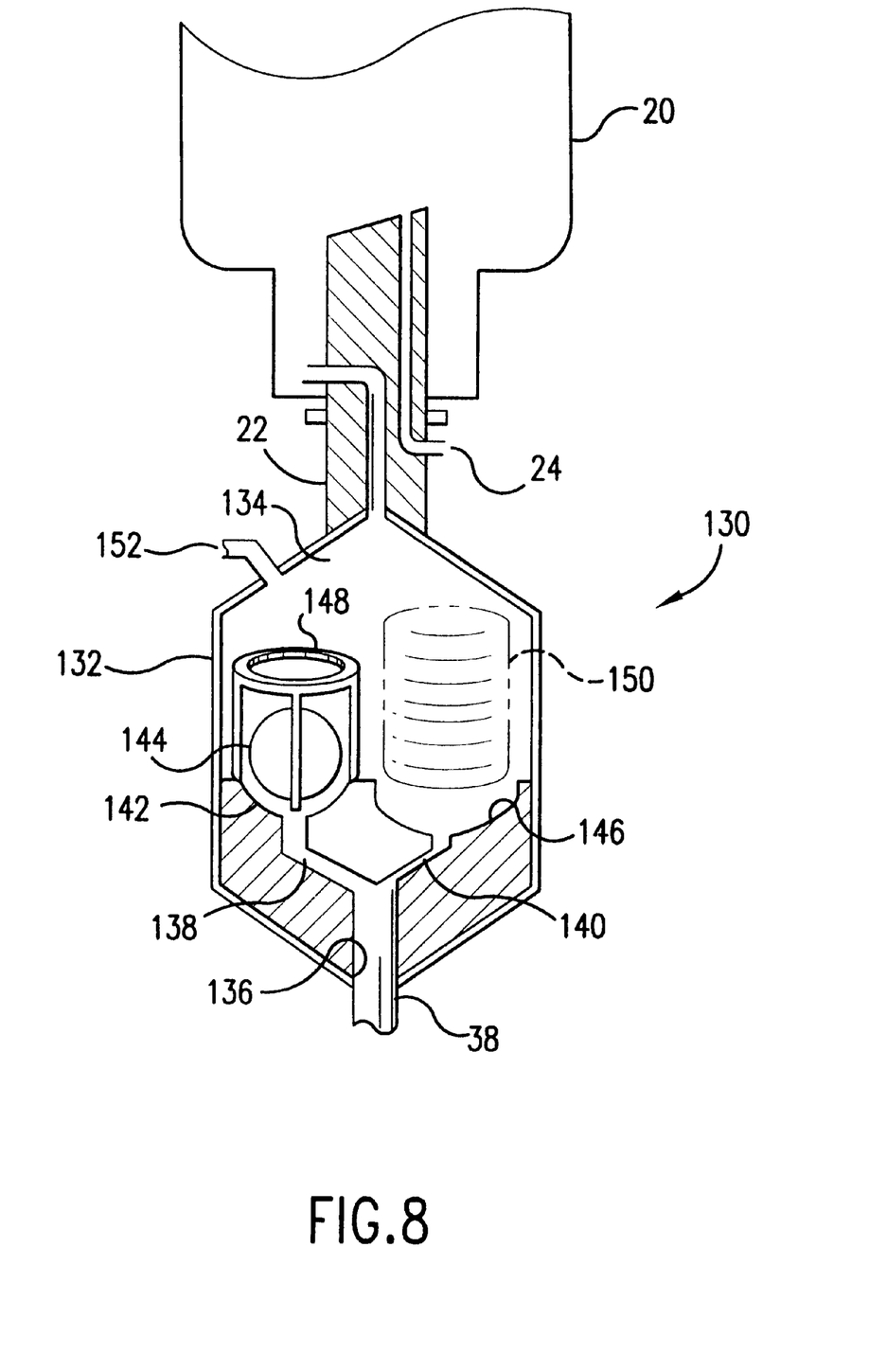
FIG. 8 is an elevation view of another embodiment of a valve for the medical dye delivery system shown in FIG. 1.
Figure 9:
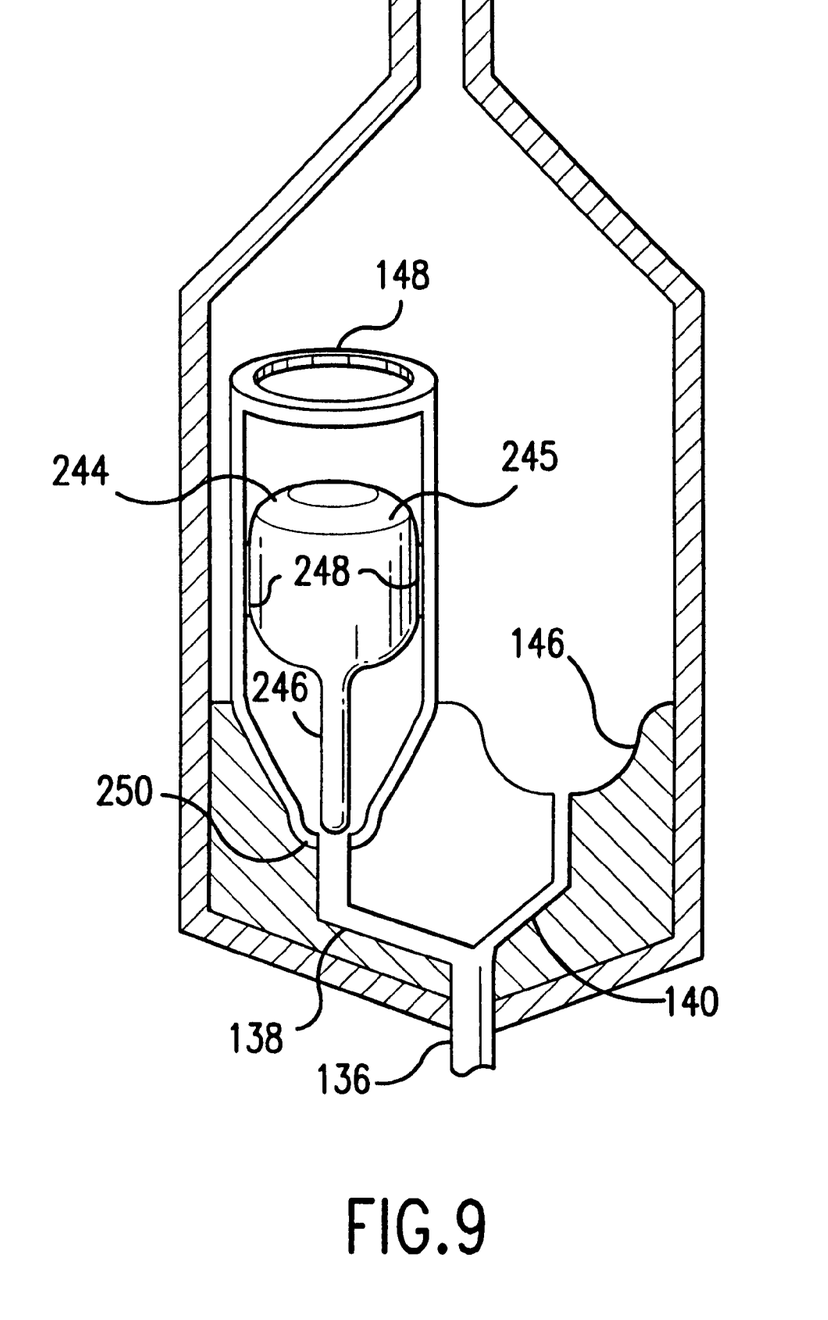
FIG. 9 is an elevation view of another embodiment of a valve for the medical dye delivery system shown in FIG. 1.

Other valve embodiments are shown in FIGS. 8 and 9. As shown in FIG. 8, valve 130 includes a valve housing 132 that defines a flotation chamber 134 for containing medical dye delivered from container 20. A passageway 136 is formed in the bottom of valve housing 132 and is connected in flow communication with conduit 38. Upstream of conduit 38, passageway 136 branches into two separate channels: a dye delivery channel 138 and a bypass channel 140. Like the embodiment shown in FIG. 2, bypass channel 140 has a cross-section that is substantially smaller than delivery channel 138 to provide restricted flow through the system, thereby increasing the force necessary to draw fluid through the system with syringe 10. This gives the operator a tactile warning of the low volume of dye remaining in the system, but still allows the operator to use this remaining dye as so desired. Bypass channel 140 may also include the bypass valve arrangements shown in FIGS. 5–7.

Delivery channel 138 is connected in flow communication with a valve seat 142, which may be conical or hemispherical in shape. As in the previous embodiments, a flotation member or ball 144 is provided in flotation chamber 134 to seat against valve seat 142, when no dye is in flotation chamber 134, and thereby block flow of air or other fluids through delivery channel 138.

Adjacent valve seat 142 is an enlarged opening 146 that leads into bypass channel 140. A small volume of dye will pool in enlarged opening 146 to facilitate flow of dye, instead of air, into bypass channel 140 when delivery channel 138 is blocked by flotation member 144.

To prevent opening 146 from accidentally being blocked by flotation member 144, flotation member 144 is placed within a cage 148 that surrounds valve seat 142. As a result, movement of flotation member 144 within flotation chamber 134 is limited so that flotation member 144 can only rest within valve seat 142 when there is no dye in flotation chamber 134.

To facilitate priming of the system, valve 130 may include an optional elastic priming member 150 that extends outwardly from the exterior of housing 132. Member 150 forms part of the peripheral wall of housing 132, but includes a substantially semi-cylindrical or hemispherical protrusion relative to the remaining, more rigid peripheral wall of housing 132. To prime the system, priming member 150 is depressed and then released to create a suction effect that draws medical dye from container 20 into flotation chamber 134.

Alternatively, selected portions of housing 132 may be made flexible to allow for depression and priming of the system, like priming member 150. The portions of housing 132 that are made flexible are selected so as to not interfere with the function and performance of flotation member 144 and bypass channel 140. For example, the upper portion of housing 132 may be flexible, while the lower portion is rigid.

As another alternative, valve 130 may include a port 152 into which a needle of a syringe is inserted. Actuating the syringe creates suction in chamber 134 to draw medical dye from container 20 into flotation chamber 134. Once priming is achieved, the syringe may be withdrawn from port 152. Port 152 preferably includes a rubber seal that allows for puncture by the syringe and subsequent closure and resealing of the port when the syringe is removed. As another alternative, any of those valves known in the art may be formed in housing 132 to allow air to enter chamber 134 when priming is desired.

Any of the above-described priming methods may be used in each of the disclosed valve embodiments to effect priming.

The embodiment shown in FIG. 9 is identical to that shown in FIG. 8 except for the geometries of the flotation member and the valve seat. As shown in FIG. 9, flotation member 244 includes a substantially cylindrical top portion 245 and an elongated, slender portion 246 extending downwardly from portion 245. In addition, the valve seat is modified to include a small, concave portion 250 that is sized to mate with the similarly-shaped end of member 246 to tightly seal delivery channel 138.

The configuration of the flotation member 244 is based on two design requirements: sufficient buoyancy in the medical dye and effective sealing of the delivery channel. Medical dye typically has a low specific gravity, but a high viscosity. Thus, the flotation member must have sufficient buoyancy to float in the medical dye, but also have sufficient weight to seal against the valve seat. The flotation member 244 shown in FIG. 9 accomplishes these design requirements by minimizing the surface areas of the flotation member and valve seat required to seal the delivery channel. Flotation member 244 also uses the greater weight of the top member 245 to press down on lower member 246 to firmly press it against valve seat 250. The total weight of member 244 may be made lighter than members required to seal a valve seat as shown, for example, in FIG. 8.

To control the orientation of flotation member 244 within cage 148, sides 248 of flotation member 244 are flattened and are spaced at close tolerances relative to the side walls of cage 148. As a result, member 246 will mate with concave portion 250 of the valve seat to tightly seal delivery channel 138.

Each of the above-described valve embodiments may be composed of plastic or any suitable materials designed for medical use.

It will be apparent to those skilled in the art that various modifications and variations can be made in the medical dye delivery system of the present invention without departing from the spirit or scope of the invention. For example, the bypass channel may be eliminated from each of the above-disclosed valve embodiments. Instead, when the operator senses increased resistance when the flotation member seats against the valve seat, the operator may terminate dye delivery and proceed with the angiography procedure or, if the remaining dye in the system is to be used, the operator may manipulate the valve (e.g. by turning the valve sideways to unseat the flotation member from the valve seat) and withdraw the remaining dye into the syringe for delivery to the patient. Thus, it is intended that the present invention cover the modifications and variations of this invention provided they come within the scope of the appended claims and their equivalents.

What is claimed is:

1. A medical dye delivery system for delivering medical dye through a system flow path to a patient, comprising:
   a medical dye container;
   a device for withdrawing medical dye from the container and directing the medical dye through the system flow path into a patient; and
   a valve having an inlet in flow communication with the medical dye container and an outlet in flow communication with the withdrawing device, the valve including a housing defining a chamber adapted for containing a volume of the medical dye, a valve seat located in the chamber and having an opening therethrough in flow communication with the outlet, and a flotation member in the chamber, the flotation member adapted for floating in the volume of medical dye and being seated against the valve seat when the chamber is substantially free of medical dye to cover the valve seat opening,
   wherein the valve further comprises a bypass channel in flow communication with the withdrawing device, the bypass channel configured to provide restricted flow relative to flow through the valve seat opening, the bypass channel permitting purging of remaining medical dye from the system flow path, and
   wherein the bypass channel comprises a slot in a wall of the valve seat forming an opening between the valve seat and the flotation member, the slot opening being substantially smaller than the valve seat opening, whereby the flotation member does not cover the slot when seated against the valve seat.

2. The delivery system of claim 1, wherein the flotation member is substantially spherical in shape.

3. The delivery system of claim 1, wherein the valve housing includes a flexible, depressible portion to permit priming of the system.

4. A medical dye delivery system for delivering medical dye through a system flow path to a patient, comprising:
   a medical dye container;
   a device for withdrawing medical dye from the container and directing the medical dye through the system flow path into a patient; and
   a valve having an inlet in flow communication with the medical dye container and an outlet in flow communication with the withdrawing device, the valve including a housing defining a chamber adapted for containing a volume of the medical dye, a valve seat located in the chamber and having an opening therethrough in flow communication with the outlet, and a flotation member in the chamber, the flotation member adapted for floating in the volume of medical dye and being seated against the valve seat when the chamber is substantially free of medical dye to cover the valve seat opening.
   wherein the valve further comprises a bypass channel in flow communication with the withdrawing device, the bypass channel configured to provide restricted flow relative to flow through the valve seat opening, the bypass channel permitting purging of remaining medical dye from the system flow path, and
   wherein the bypass channel includes a bypass valve disposed therein for providing the restricted flow through the bypass channel.

5. The delivery system of claim 4, wherein the bypass channel includes an inlet upstream of the valve seat opening and an outlet downstream of the valve seat opening.

6. The delivery system of claim 5, wherein the bypass valve comprises a valve seat and a valve member biased against the valve seat with a predetermined biasing force.

7. The delivery system of claim 4, wherein the bypass channel has a cross-section substantially smaller than the valve seat opening.

8. The delivery system of claim 4, wherein the bypass valve includes a flexible member with an opening therethrough that is substantially smaller than the valve seat opening.

9. A medical dye delivery system for delivering medical dye through a system flow path to a patient, comprising:
   a medical dye container;
   a device for withdrawing medical dye from the container and directing the medical dye through the system flow path into a patient; and
   a valve having an inlet in flow communication with the medical dye container and an outlet in flow communication with the withdrawing device, the valve including a housing defining a chamber adapted for containing a volume of the medical dye, a valve seat located in the chamber and having an opening therethrough in flow communication with the outlet, and a flotation member in the chamber, the flotation member adapted for floating in the volume of medical dye and being seated against the valve seat when the chamber is substantially free of medical dye to cover the valve seat opening.
   wherein the valve further comprises a bypass channel in flow communication with the withdrawing device, the bypass channel configured to provide restricted flow relative to flow through the valve seat opening, the bypass channel permitting purging of remaining medical dye from the system flow path, and
   wherein the bypass channel has an opening downstream of the valve seat opening and an opposite opening in selective flow communication with external air, the bypass channel having a bypass valve for selectively permitting external air to enter the bypass channel.

10. A medical dye delivery system for delivering medical dye through a system flow path to a patient, comprising:

a medical dye container;

a device for withdrawing medical dye from the container and directing the medical dye through the system flow path into a patient;

a valve having an inlet in flow communication with the medical dye container and an outlet in flow communication with the withdrawing device, the valve including a housing defining a chamber adapted for containing a volume of the medical dye, a valve seat located in the chamber and having an opening therethrough in flow communication with the outlet, and a flotation member in the chamber, the flotation member adapted for floating in the volume of medical dye and being seated against the valve seat when the chamber is substantially free of medical dye to cover the valve seat opening;

wherein the flotation member comprises a first portion and an elongated second portion extending from the first portion, the second portion having a cross-section that is smaller in dimension than the first portion, and an end of the second portion being shaped to seat against the valve seat to close the valve seat opening;

wherein the valve further comprises a bypass channel in flow communication with the withdrawing device the bypass channel permitting purging of remaining medical dye from the system flow path; and wherein the bypass channel comprises a slot in a wall of the valve seat forming an opening between the valve seat and the flotation member, the slot opening being substantially smaller than the valve seat opening, whereby the flotation member does not cover the slot when seated against the valve seat.

11. A medical dye delivery system for delivering medical dye through a system flow path to a patient, comprising:

a medical dye container;

a device for withdrawing medical dye from the container and directing the medical dye through the system flow path into a patient; and a valve having an inlet in flow communication with the medical dye container and an outlet in flow communication with the withdrawing device, the valve including a housing defining a chamber adapted for containing a volume of the medical dye, a valve seat located in the chamber and having an opening therethrough in flow communication with the outlet, and a flotation member in the chamber, the flotation member adapted for floating in the volume of medical dye and being seated against the valve seat when the chamber is substantially free of medical dye to cover the valve seat opening;

wherein the flotation member comprises a first portion and an elongated second portion extending from the first portion, the second portion having a cross-section that is smaller in dimension than the first portion, and an end of the second portion being shaped to seat against the valve seat to close the valve seat opening; and wherein the valve further comprises a cage disposed within the chamber and surrounding the valve seat, the flotation member disposed within the cage to limit movement of the flotation member within the chamber.

12. A medical dye delivery system for delivering medical dye through a system flow path to a patient, comprising:

a medical dye container;

a device for withdrawing medical dye from the container and directing the medical dye through the system flow path into a patient; and a valve having an inlet in flow communication with the medical dye container and an outlet in flow communication with the withdrawing device, the valve including a housing defining a chamber adapted for containing a volume of the medical dye, a valve seat located in the chamber and having an opening therethrough in flow communication with the outlet, and a flotation member in the chamber, the flotation member adapted for floating in the volume of medical dye and being seated against the valve seat when the chamber is substantially free of medical dye to cover the valve seat opening, wherein the valve further comprises a port formed in the valve housing in selective flow communication with the flotation chamber, the port selectively opened and closed to allow priming of the system by an external source.

13. A valve for a medical dye delivery system, comprising:

a housing having an inlet and an outlet and defining a chamber adapted for containing a volume of medical dye;

a valve seat located in the chamber and having an opening therethrough in flow communication with the outlet;

a flotation member in the chamber, the flotation member adapted for floating in the volume of medical dye and being seated against the valve seat when the chamber is free of medical dye to cover the valve seat opening; and a bypass channel in flow communication with the outlet, the bypass channel configured to provide restricted flow relative to flow through the valve seat opening, the bypass channel permitting purging of remaining medical dye from the delivery system, wherein the bypass channel comprises a slot in a wall of the valve seat forming an opening between the valve seat and the flotation member, the slot opening being substantially smaller than the valve seat opening, whereby the flotation member does not cover the slot when seated against the valve seat.

14. The valve of claim 13, wherein the bypass channel includes an inlet upstream of the valve seat opening and an outlet downstream of the valve seat opening.

15. The valve of claim 13, wherein the flotation member is substantially spherical in shape.

16. The valve of claim 13, wherein the valve housing includes a flexible, depressible portion to permit priming of the system.

17. A valve for a medical dye delivery system, comprising:

a housing having an inlet and an outlet and defining a chamber adapted for containing a volume of medical dye;

a valve seat located in the chamber and having an opening therethrough in flow communication with the outlet;

a flotation member in the chamber, the flotation member adapted for floating in the volume of medical dye and being seated against the valve seat when the chamber is free of medical dye to cover the valve seat opening; and a bypass channel in flow communication with the outlet, the bypass channel configured to provide restricted flow relative to flow through the valve seat opening, the bypass channel permitting purging of remaining medical dye from the delivery system, wherein the bypass channel includes a bypass valve disposed therein for providing the restricted flow through the bypass channel.

18. The valve of claim 17, wherein the bypass valve comprises a valve seat and a valve member biased against the valve seat with a predetermined biasing force.

19. The valve of claim 17, wherein the bypass channel has a cross-section substantially smaller than the valve seat opening.

20. The valve of claim 17, wherein the bypass valve includes a flexible member with an opening therethrough that is substantially smaller than the valve seat opening.

21. A valve for a medical dye delivery system, comprising:
   a housing having an inlet and an outlet and defining a chamber adapted for containing a volume of medical dye;
   a valve seat located in the chamber and having an opening therethrough in flow communication with the outlet;
   a flotation member in the chamber, the flotation member adapted for floating in the volume of medical dye and being seated against the valve seat when the chamber is free of medical dye to cover the valve seat opening; and
   a bypass channel in flow communication with the outlet, the bypass channel configured to provide restricted flow relative to flow through the valve seat opening, the bypass channel permitting purging of remaining medical dye from the delivery system,
   wherein the bypass channel has an opening downstream of the valve seat opening and an opposite opening in selective flow communication with external air, the bypass channel having a bypass valve for selectively permitting external air to enter the bypass channel.

22. A valve for a medical dye delivery system, comprising:
   a housing having an inlet and an outlet and defining a chamber adapted for containing a volume of medical dye;
   a valve seat located in the chamber and having an opening therethrough in flow communication with the outlet;
   a flotation member in the chamber, the flotation member adapted for floating in the volume of medical dye and being seated against the valve seat when the chamber is free of medical dye to cover the valve seat opening; and
   a bypass channel in flow communication with the outlet, the bypass channel configured to provide restricted flow relative to flow through the valve seat opening, the bypass channel permitting purging of remaining medical dye from the delivery system,
   wherein the flotation member comprises a first portion and an elongated second portion extending from the first portion, the second portion having a cross-section that is smaller in dimension than the first portion, and an end of the second portion being shaped to seat against the valve seat to enclose the valve seat opening.

23. The valve of claim 22, wherein the valve further comprises a cage disposed within the chamber and surrounding the valve seat, the flotation member disposed within the cage to limit movement of the flotation member within the chamber.

24. A valve for a medical dye delivery systems comprising:
   a housing having an inlet and an outlet and defining a chamber adapted for containing a volume of medical dye;
   a valve seat located in the chamber and having an opening therethrough in flow communication with the outlet;
   a flotation member in the chamber, the flotation member adapted for floating in the volume of medical dye and being seated against the valve seat when the chamber is free of medical dye to cover the valve seat opening; and
   a bypass channel in flow communication with the outlet, the bypass channel configured to provide restricted flow relative to flow through the valve seat opening, the bypass channel permitting purging of remaining medical dye from the delivery system,
   wherein the valve further comprises a port formed in the valve housing in selective flow communication with the flotation chamber, the port selectively opened and closed to allow priming of the system by an external source.

25. A valve for a fluid delivery system, comprising:
   a housing having an inlet and an outlet and defining a chamber adapted for containing a volume of fluid;
   a valve seat located in the chamber and having an opening therethrough in flow communication with the outlet;
   a flotation member in the chamber, the flotation member adapted for floating in the volume of fluid, the flotation member comprising a first portion and a second portion attached to the first portion, the second portion having a cross-section smaller in dimension than the first portion, the second portion adapted to be seated against the valve seat when the chamber is free of fluid to close the valve seat opening;
   a bypass channel in flow communication with the outlet, the bypass channel configured to provide restricted flow relative to the flow through the valve seat opening, the bypass channel permitting purging of remaining medical dye from the delivery system; and
   wherein the bypass channel comprises a slot in a wall of the valve seat forming an opening between the valve seat and the flotation member, the slot opening being substantially smaller than the valve seat opening, whereby the flotation member does not cover the slot when seated against the valve seat.

* * * * *